United States Patent [19]

Lewis et al.

[11] Patent Number: 5,308,773
[45] Date of Patent: May 3, 1994

[54] NON-AZO 1,8-NAPHTHALIMIDE DYES FOR THE DETECTION AND QUANTITATION OF A PARAMAGNETIC METAL CATION IN A NON-AQUEOUS MEDIUM

[75] Inventors: David E. Lewis, Brookings; Ronald E. Utecht, Volga, both of S. Dak.; Millard M. Judy; J. Lester Matthews, both of Dallas, Tex.

[73] Assignee: MicroBioMed Corp., Dallas, Tex.

[21] Appl. No.: 977,508

[22] Filed: Nov. 16, 1992

[51] Int. Cl.$^5$ .................. G01N 33/20; C07D 221/06
[52] U.S. Cl. ................................. 436/73; 436/82; 546/100
[58] Field of Search .............. 436/82, 73; 250/302; 546/100

[56] References Cited

U.S. PATENT DOCUMENTS

| | | | |
|---|---|---|---|
| 2,415,373 | 2/1947 | Scalera et al. | 546/100 |
| 3,843,325 | 10/1974 | Schmitt et al. | 436/82 |
| 3,965,350 | 6/1976 | Molina | 250/302 |
| 4,200,752 | 4/1980 | Bertelson | |
| 4,876,206 | 10/1989 | Sayer | 436/82 |
| 5,126,272 | 6/1992 | Kingston, Jr. et al. | 436/82 |

FOREIGN PATENT DOCUMENTS 753104 3/1933 France .

OTHER PUBLICATIONS

Homan, et al., "A fluorescence quenching technique for the measurement of paramagnetic ion concentrations . . .", Biochimica et Biophysica Acta 812 (1985) 485-492.
Kowk, et al., "The interaction of paramagnetic ions chelated to ATP with pyridoxal analogues", *Eur. J. Biochem.* 199, 157-162 (1991).
Nag-Chaudhuri, et al., "External Heavy-Atom Spin-Orbital Coupling Effect. II. Comments on the Effect of Ferric Acetylacetonate . . . ", *Journal of Chemical Physics*, vol. 38, No. 8, Apr. 15, 1963.
Winefordner, et al., "Luminescence Spectrometry in Analytical Chemistry", Chemical Analysis, vol. 38, pp. Preface, 64-65.
Hercules, et al. "*Fluorescence and Phosphorescence Analysis*", Chapter 1, pp. Preface, 32-33.
Becker, *Theory and Interpretation of Fluorscence and Phosphorescence*, Chapter 13, "Molecular Complexes", pp. 190-209.

*Primary Examiner*—James C. Housel
*Assistant Examiner*—Rachel Freed
*Attorney, Agent, or Firm*—Winstead Sechrest & Minick

[57] ABSTRACT

The use of a class of non-azo 1,8-naphthalimide dyes for the detection and quantitation of a paramagnetic metal cation in a non-aqueous medium and some of the dyes that will complex with a paramagnetic metal cation. The concentration of the paramagnetic metal cation is determined by monitoring differences in the detected fluorescent emission spectra of the non-azo 1,8-naphthalimide dye solution when it is mixed with paramagnetic metal cations present in the non-aqueous medium. The detected fluorescent emission spectra will vary in relation to the presence or amount of the paramagnetic metal cation in the mixture.

18 Claims, 4 Drawing Sheets

| R= | R'= |
|---|---|
| $(CH_2)_3CH_3$ | $(CH_2)_2NH_2$ |
| $(CH_2)_5CH_3$ | $(CH_2)_2OH$ |
| $(CH_2)_5CH_3$ | $(CH_2)_2NH_2$ |
| $(CH_2)_7CH_3$ | $(CH_2)_2NH_2$ |
| $(CH_2)_8CH_3$ | $(CH_2)_2NH_2$ |
| $(CH_2)_9CH_3$ | $(CH_2)_2NH_2$ |
| $(CH_2)_{11}CH_3$ | $(CH_2)_2NH_2$ |
| $(CH_2)_{13}CH_3$ | $(CH_2)_2NH_2$ |
| $(CH_2)_{15}CH_3$ | $(CH_2)_2NH_2$ |
| $(CH_2)_{17}CH_3$ | $(CH_2)_2NH_2$ |

*FIG. 7*

NON-AZO 1,8-NAPHTHALIMIDE DYES FOR THE DETECTION AND QUANTITATION OF A PARAMAGNETIC METAL CATION IN A NON-AQUEOUS MEDIUM

TECHNICAL FIELD OF THE INVENTION

Method of using a predominantly hydrophobic non-azo 1,8-naphthalimide dye and its mixture in the detection and quantitation of a paramagnetic metal cations in a non-aqueous medium, more specifically, the present invention relates to the use of a predominantly hydrophobic non-azo N-alkyl-4-alkylamino-1,8-naphthalimide dye and its mixture in the detection of a paramagnetic metal cation in a lubricant.

BACKGROUND OF THE INVENTION

In any mechanical system, moving parts are subjected to wear. Despite the fact that mechanical systems are designed and lubricated in an effort to minimize wear, wear will always exist. It is important to be able to assess engine wear and avoid unpredicted equipment failure. The presence of an excessive amount of wear metal in an engine's lubricant indicates either lubricant failure or an impending mechanical failure of the system.

Spectrometric oil analysis programs (SOAP) can serve to identify problem areas before the loss of equipment to catastrophic failure by monitoring the concentration of wear metals suspended in an engine's lubricant. The success of the SOAP system is attested to by the required routine analysis of the lubricants of all aircraft and military mechanical systems. In addition, voluntary lubricant analysis is commonplace in fleet vehicles.

At present atomic emission methods are used to detect metal ions for military samples. The advantage of this methodology is that it can detect 21 elements (Fe, Cr, Cu, Ni, Mn, Ag, Al, Mg, Pb, Si, Na, Sn, Ti, V, Cd, Ca, P, B, Mo, Zn, and Ba) in the 1-1500 ppm range simultaneously. Problems associated with this methodology are: Its inability to detect metals in particles larger than 10 microns; the expense of the equipment required; the instability of the atomic absorption spectrophotometer's flame when testing hydraulic fluids; and the inability to assign oxidation levels to any wear metals present in the oil.

There are two major components to wear in any mechanical system, mechanical wear and corrosive wear. Mechanical wear is simply the scraping of metal particles from a surface while corrosive wear is the oxidation of metal on the surface giving a species that easily crumbles from the surface often without mechanical contact. Magnesium alloys are particularly sensitive to corrosive wear. Atomic admission spectra detect fine metal particles, colloidal suspensions, and discrete ions to the same extent. Lacking the speciation between these forms of the metals precludes the assessment of wear due to corrosion and that due to mechanical abrasion.

Based on the foregoing, a need has arisen for a faster, less expensive, more accessible method of oil analysis that would be practical for both large and small fleets of vehicles.

SUMMARY OF THE INVENTION

According to the teachings of the present invention, new non-azo 1,8-naphthalimide dyes, either monomeric or dimeric, are used to detect and quantitate paramagnetic metal cations in non-aqueous solutions. The synthesis and characterization of some of these dyes is described in U.S. patent application Ser. No. 07/854,416, filed Mar. 19, 1992, and entitled "Non-Azo Naphthalimide Dyes and Uses for Same," the entire contents and disclosure of which are hereby specifically incorporated by reference. Additional dyes are described below.

Accordingly, it is an object of the present invention to provide a quick and accessible method for the detection and quantitation of a paramagnetic metal cation in a non-aqueous medium without having to pretreat the metal. Thus, the method can be used for the detection and quantitation of a paramagnetic cation in the presence of an elemental metal.

Another object of the present invention is to provide a quick and accessible method for the detection of a paramagnetic cation in lubricants of mechanical systems.

Yet another object of the present invention is to provide a quick and accessible method for the detection of a paramagnetic cation in oil.

A further object of the present invention is the synthesis of new non-azo 1,8-naphthalimide dyes that complex with a paramagnetic metal cation and thereby change their fluorescent emission spectra.

Other objects, advantages and novel features of the present invention will become apparent from the following detailed description of the invention.

BRIEF DESCRIPTION OF THE DRAWINGS

For a more complete understanding of the present invention, and the advantages thereof, reference is now made to the following descriptions taken in conjunction with the accompanying drawings, in which.

DETAILED DESCRIPTION OF THE INVENTION

The present invention pertains to the use of a non-azo 1,8-naphthalimide dye, either monomeric or dimeric, to detect and quantitate a paramagnetic metal cation in a non-aqueous medium, such as an oil or a lubricant. There is no requirement of pretreating the metal in the medium. In fact, the method of the present invention can be used to detect and quantitate a paramagnetic metal cation in the presence of an elemental metal.

Broadly, the present invention pertains to the use of a non-azo 1,8-naphthalimide dye for the detection and quantitation of a paramagnetic metal cation in a non-aqueous medium by monitoring differences in the fluorescent emission spectra of the dye upon formation of a complex between the dye and the paramagnetic metal cation. The method used to quantitate the paramagnetic metal cations involves the following steps: mixing a non-azo 1,8-naphthalimide dye with a non-aqueous medium containing the paramagnetic metal cations to be quantitated; irradiating the mixture with a fluorescent light source, and monitoring the differences in the detected emission spectra of the dye that are dependent upon the presence and quantity of paramagnetic metal cations.

Some of the non-azo-1,8-naphthalimide dyes suitable for the quantitation of a paramagnetic metal cation are non-azo N-substituted-1,8-naphthalimide compounds bearing a heteroatom directly linked to the 4-position and having an aliphatic amine attached to the heteroatom.

Additional non-azo 1,8-naphthalimide dyes that can be used for detecting and quantitating paramagnetic metals in non-aqueous solutions are fully described in U.S. Pat. No. 5,235,045 and have been incorporated herein by reference. These dyes include naphthalimide rings bearing substituents at the 3 and 4 positions with the group at the 3 position capable of functioning as a leaving group. More specifically, some of the dyes utilized in the present invention pertain to 3-substituted-4-hydroxy-N-substituted-1,8-naphthalimides, 3-substituted-4-amino-1,8-naphthalimides, and 3,4-disubstituted-1,8-naphthalimides with pendant alkyl groups functionalized with halogens, with ionic groups such as carboxylates and phosphonates, and with heterocyclic groups such as pyridines, etc.

The detection and quantitation of a paramagnetic metal cation in non-aqueous medium may also utilize the dimeric naphthalimide ring systems described in U.S. Pat. No. 5,235,045, incorporated herein by reference. The dimeric naphthalimide ring systems utilized in the present invention have one disubstituted ring and one unsubstituted ring, and every ring system bears substituents at the 3 and 4 positions with the group at the 3 position capable of functioning as a leaving group. More particularly, the dimeric dyes utilized pertain to bis-(3,4-disubstituted-1,8-naphthalimides) with pendant alkyl groups functionalized with halogens, with ionic groups such as carboxylates and phosphonates, and with heterocyclic groups such as pyridines, etc. The site of attachment of the alkylene linker between the two naphthalimide monomeric units is through the heterocyclic nitrogen atom of both naphthalimide ring systems, through the heterocyclic nitrogen atom of one naphthalimide monomeric unit to the 4-alkylamino nitrogen atom of the second naphthalimide monomeric unit, or through the 4-alkylamino nitrogen of both naphthalimide monomeric units.

The quantitation of paramagnetic metal cations in a non-aqueous medium, such as oil, is performed by reacting one of the dyes, described above, with a paramagnetic cation in an oil sample and quantitating the metal-dye complex formation by measuring the fluorescent emission ratio of 490 to 520 nm using an excitation wavelength of about 450 nm. As used herein, the terms "fluorescence" and "luminescence" are used interchangeably in all respects. This fluorescence ratio is dependent on the concentration of metal cation in the medium and can be used to calculate the paramagnetic metal cation concentrations in an oil sample. The fluorescence ratio is converted to the paramagnetic metal cation concentration by comparing it with fluorescence ratios on a calibration curve generated by reacting the dyes with oil standards containing known quantities of paramagnetic metal cation.

Figure 1:
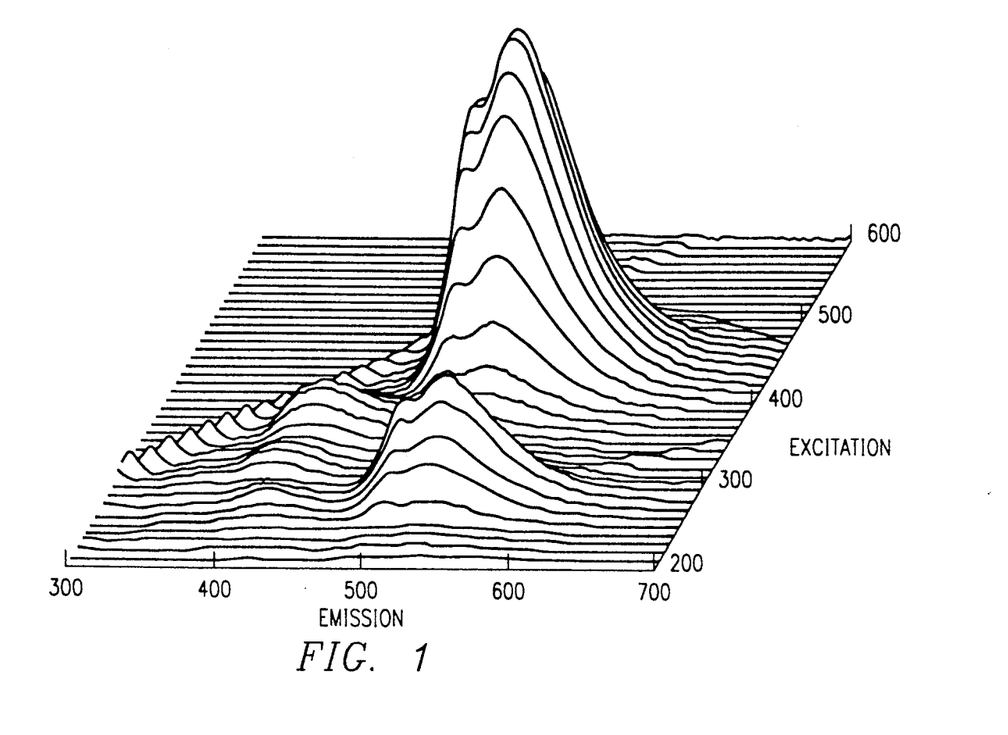
FIG. 1 shows a fluorescence spectrum of 5 $\mu$M N-hexadecyl-4-[(2'-aminoethyl)amino]-1,8-naphthalimide in metal free isopropyl alcohol.

FIG. 1 shows a fluorescence or luminescence spectrum of 5 $\mu$M N-hexadecyl-4-[(2'-aminoethyl)amino]-1,8-naphthalimide in metal free isopropyl alcohol. The maximum fluorescence is 50.6. The major peak has an excitation maximum of 450 nm and an emission maximum of 527 nm. The secondary peak with an excitation maximum of 290 nm has the same emission profile as the major peak.

Figure 2:
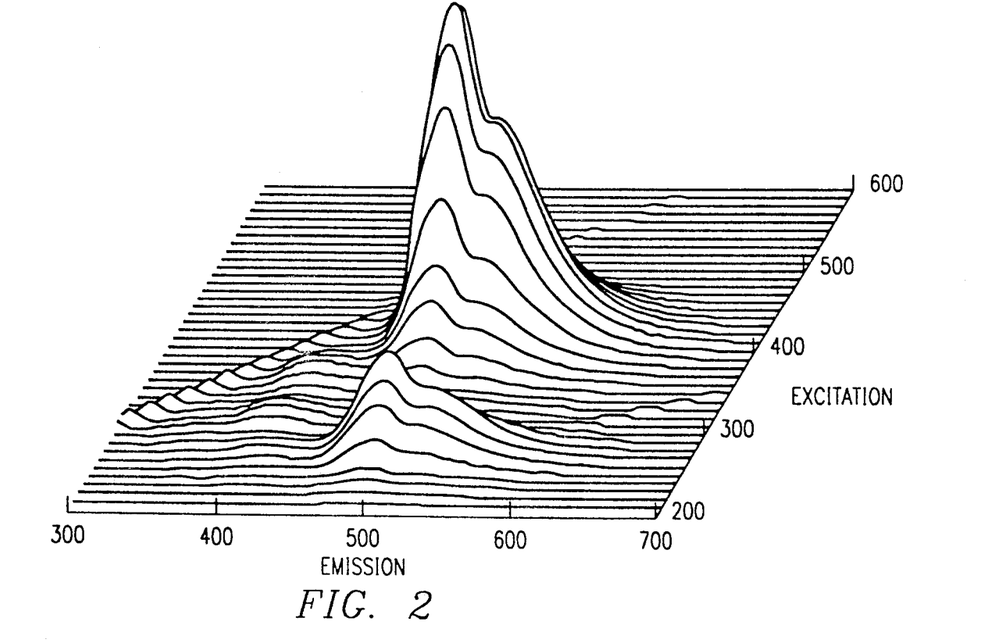
FIG. 2 shows a fluorescence spectrum of 5 $\mu$M N-hexadecyl-4-[(2'-aminoethyl)amino]-1,8-naphthalimide in isopropyl alcohol containing 5 $\mu$M Cu (II) (0.32 ppm)

Upon the addition of 5 $\mu$M $Cu^{2+}$, from hydrated $Cu(NO_3)_2$, the fluorescence intensity increases to 96.4 and the shape of the fluorescence curve is altered dramatically as shown in FIG. 2. The major peak has an excitation maximum of 420 nm and an emission maximum of 490 nm. The secondary peak with an excitation maximum of 290 nm has the same emission profile as the major peak. Upon the addition of copper, the intensity of the fluorescence of the major peak (excitation at 450 nm) increases; wavelength shifts are evident with the major peak showing a change from a maxima at 527 nm with a shoulder at 493 nm to a maxima at 493 nm with a shoulder at 527 nm. This same change is also evident in the peaks produced by excitation at 290 nm. This change in peak ratios can serve to indicate the presence and concentration of $Cu^{2+}$ ions Table 1 summarizes the ratios of these two peaks with various metal concentrations in $\mu$M.

TABLE 1

| Change in emission peak ratios with $[Cu^{2+}]$ ($EM_{527}/EM_{493}$) | | |
|---|---|---|
| $[Cu^{2+}]$ | 450 nm excitation | 290 nm excitation |
| 0 | 1.47 | 1.32 |
| 0.5 | 1.44 | 1.32 |
| 2 | 1.33 | 1.27 |
| 4 | 1.29 | 1.19 |
| 6 | 1.20 | 1.01 |
| 7.5 | 0.98 | 0.90 |
| 200 | 0.76 | 0.76 |

The length of the alkyl chain did not seem to have an effect on the ability of the $Cu^{2+}$ to influence the spectrum. The presence of 50% (v/v) water destroyed the complex. The use of DMF as the solvent gave spectral results identical to those obtained with isopropyl alcohol.

Other transition metals ($Fe^{3+}$, $CO^{2+}$, $CR^{3+}$, and $Mn^{2+}$) displayed substantially the same behavior. The exact surface of the spectrum appeared to depend on the identity of the metal ions and a deconvolution of the surface may serve to not only quantify the ions present but also to identify those ions. $Al^{3+}$ and $Zn^{2+}$ induced changes at least an order of magnitude smaller but of the same nature as produced by the transition metals.

Figure 6:
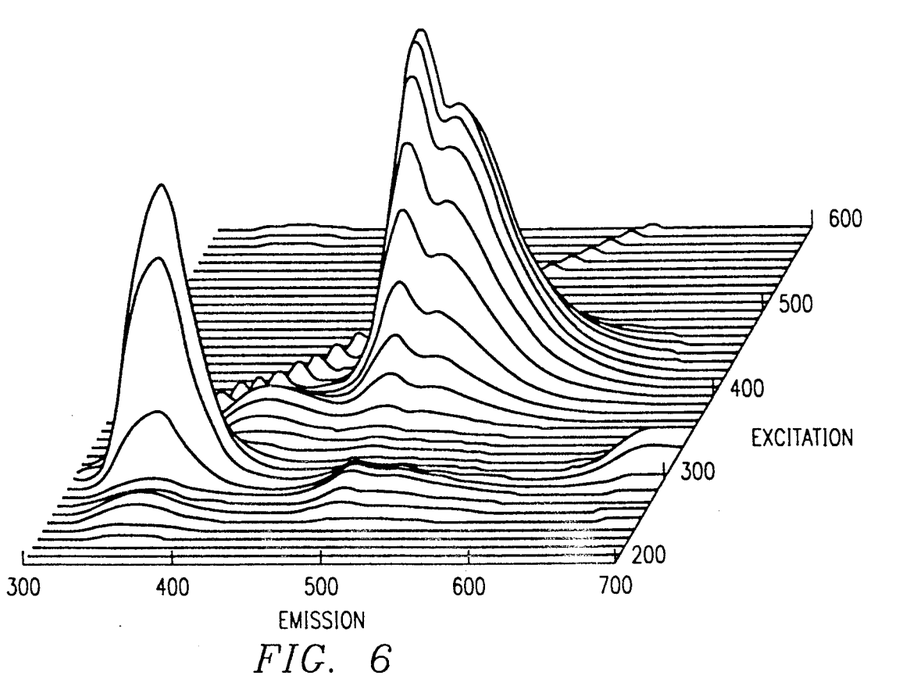
FIG. 6 shows a fluorescence spectrum of 5 $\mu$M N-hexadecyl-4-[(2'-aminoethyl)amino]-1,8-naphthalimide in isopropyl alcohol containing 5 $\mu$M Ce (III)

$Ce^{3+}$ (from hydrated $CeCl_3$) also influenced the spectrum, but in a way that was subtly different than the way transition metals influenced the spectrum. The fluorescence spectrum is shown in FIG. 6. The major peak behaved in the same manner as with transition metals but a new peak, excitation 310 nm, emission 720 nm, had appeared. The most dramatic change in the spectrum was the increase in fluorescence at an emission wavelength of 493 nm with respect to emission at 520 nm along with a general increase in fluorescent intensity.

This general change in spectral intensity was produced by all paramagnetic metal cations tested to date, $Fe^{3+}$, $Fe^{2+}$, $Cr^{3+}$, $Cu^{2+}$, $Ni^{2+}$, $Ce^{3+}$, and $Mn^{2+}$. Non-paramagnetic metal cations tested ($Zn^{2+}$, $Al^{3+}$, and $Pb^{2+}$) showed no effect on the fluorescent emission of the dye.

The stoichiometry of the metal-dye complex was explored by a Job's Law plot of the fluorescence ratio of the complex versus the concentration of $Cu^{2+}$. The inflection point was seen at 1:1 mole ratio of dye to metal giving a stoichiometry of 1 dye: 1 $Cu^{2+}$.

Figure 3:
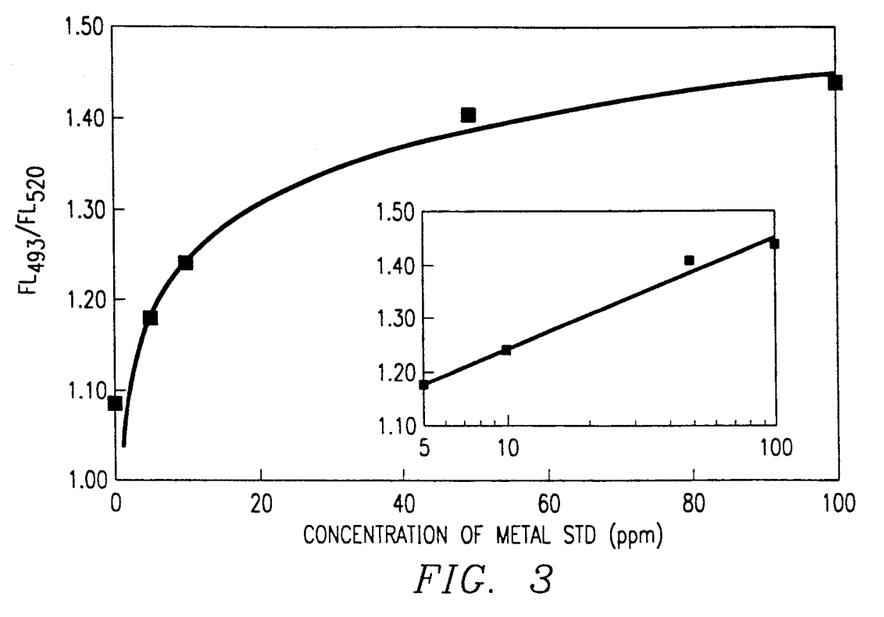
FIG. 3 is a calibration curve for copper metal analysis.

FIG. 3 shows a calibration curve demonstrating the response of the dye to varying concentrations of Cu (II) paramagnetic metal cation in the oil standards prepared by Constan Oil Company.

Ferrocene was found to influence the spectrum of the dyes in the same manner as the simple paramagnetic ions. However, the addition of disodium ethylenediaminetetracetic acid (EDTA) did not influence the fluorescent spectrum in either the presence of absence of metal ions.

Figure 4:
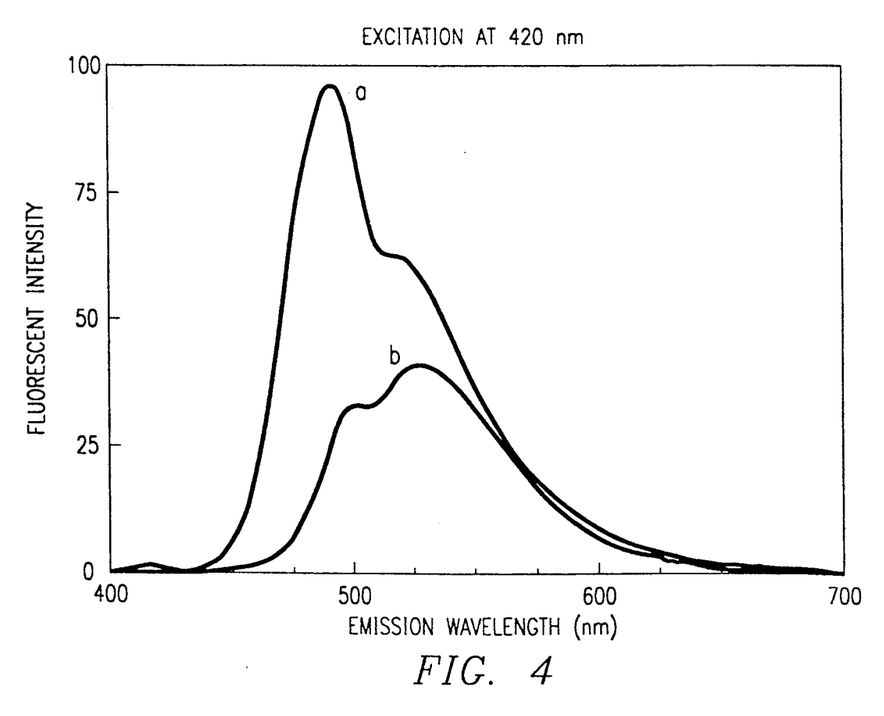
FIG. 4 shows the influence of 5 $\mu$M Cu (II) on the fluorescence spectrum of 5 $\mu$M N-hexadecyl-4-[(2'-aminoethyl)amino]-1,8-naphthalimide at the excitation of 420 nm.

FIG. 4 highlights the changes in emission intensity of 5 $\mu$M of N-hexadecyl-4-[(2'-aminoethyl) amino]-1,8-naphthalimide with an excitation wavelength of 420 nm in the presence ("a") and absence ("b") of 5 $\mu$M Cu (II). The ratio of the emission at 490 nm is directly proportional to the logarithm of the Cu (II) concentration. Again this ration may be used to calculate metal ion concentration. Other paramagnetic metal ions give substantially the same shift and can also be quantitated in the same manner. The secondary peak with an excitation wavelength of 290 nm can also be used to quantitate d-block paramagnetic ions. This secondary peak is suppressed by f-block elements so it is not suitable for the determination of these ions.

Figure 5:
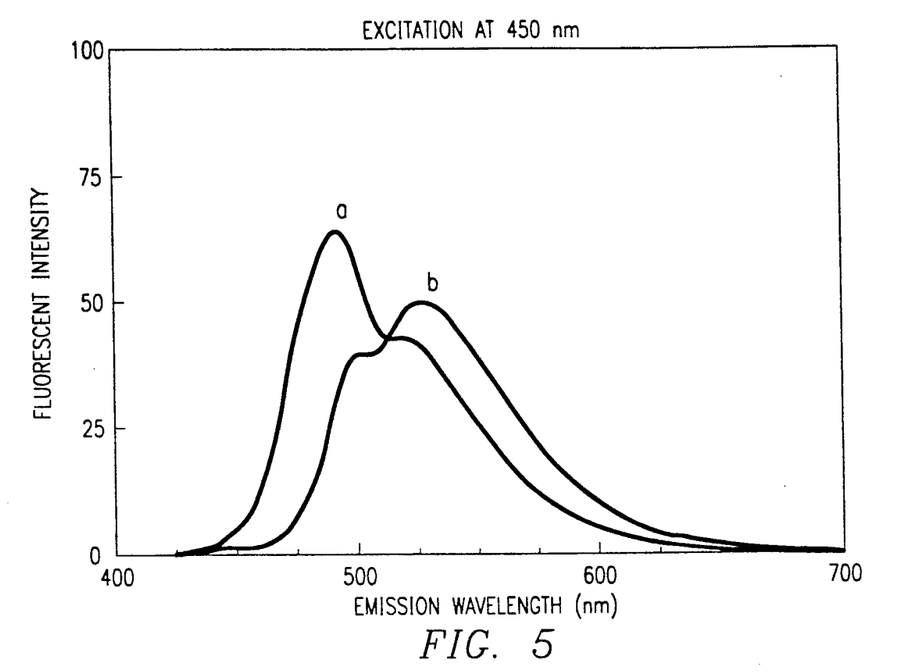
FIG. 5 shows the influence of 5 $\mu$M Cu (II) on the fluorescence spectrum of 5 $\mu$M N-hexadecyl-4-[(2'-aminoethyl)amino]-1,8-naphthalimide at the excitation of 450 nm.

FIG. 5 highlights the changes in emission intensity of 5 $\mu$M of N-hexadecyl-4-[(2'-aminoethyl) amino]-1,8-naphthalimide with an excitation wavelength of 450 nm in the presence ("a") and absence ("b") of 5 $\mu$M Cu (II). The ratio of the emission at 490 and 527 nm is directly proportional to the logarithm of the Cu (II) concentration and can be used to calculate the concentration of the metal ion.

FIG. 6 shows the total fluorescence or luminescence spectrum of the N-hexadecyl-4-[(2'-aminoethyl)amino]-1,8-naphthalimide dissolved in isopropyl alcohol to a concentration of 5 $\mu$M after the addition of 5$\mu$M Ce (III) (from hydrated $CeCl_3$). The major peak has an excitation maximum of 440 nm and an emission maximum of 490 nm. The change in the major peak upon the addition of Ce (III) is very similar to the change upon the addition of Cu (II). The secondary peak with an excitation maximum of 290 nm has dramatically decreased when compared to the major peak. This behavior is only seen with cerium, a lanthanide element. The fluorescent peak with an excitation of 310 nm and an emission of 380 nm is due to the fluorescence of the lanthanide element.

Figure 7:
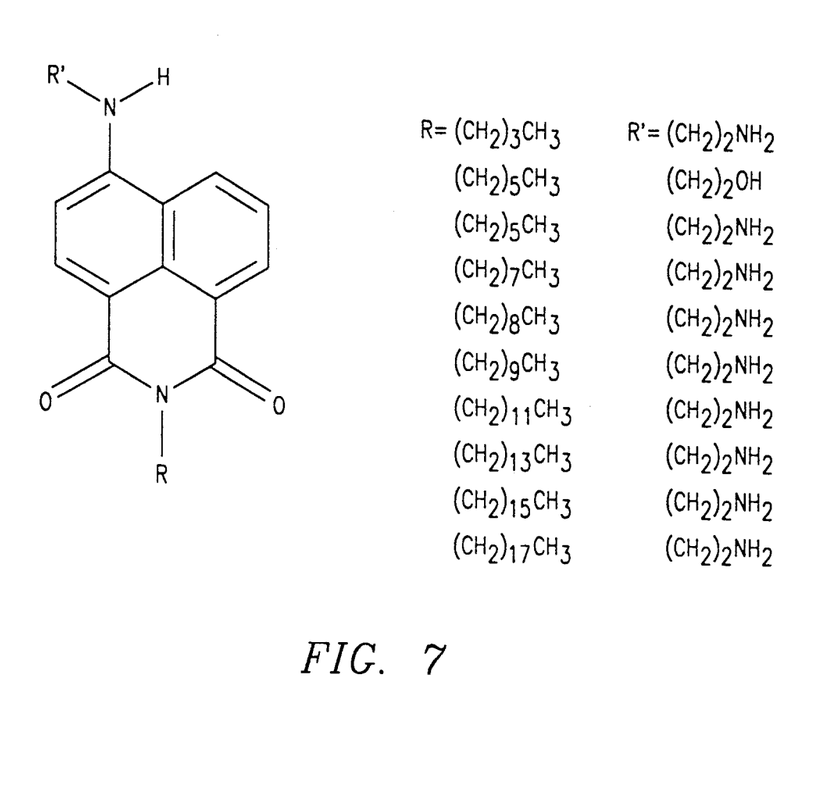
FIG. 7 shows the structural formula of some of the dyes used in this invention.

FIG. 7 shows the structural formula of some of the N-alkyl-4-alkylamino-1,8-naphthalimide dyes used to detect and quantitate paramagnetic metal cations. Non-azo 1,8-Naphthalimide dyes, represented by the generic formula given in FIG. 7, that are suitable for quantitating a paramagnetic metal cation include those dyes wherein R is an aliphatic alkyl group having C=4 to C=18; and R' is $(CH_2)_2NH_2$ or $(CH_2)_2OH$. Preferred embodiments of the present invention include dyes wherein the R is an aliphatic hexyl, hexadecyl, or octadecyl alkyl group. The most preferred embodiment of the present invention, set forth in Example 1 below, utilizes N-hexadecyl-4-[(2'aminoethyl)amino]-1,8-naphthalimide to quantitate paramagnetic metal cations.

The invention is further defined by reference to the following examples, which are intended to be illustrative and not limiting.

EXAMPLE 1

General procedure for the synthesis of the 1,8-naphthalimide dyes of FIG. 7

4-Chloro-1,8-naphthalic anhydride (technical grade, approximately 90% pure, purchased from Janssen Chimia) was recrystallized from toluene prior to use. This gave a material which was at least 95% pure, with the remaining 5% being the 3-chloro isomer. The recrystallized anhydride (1 equivalent) was placed in a round-bottomed flask equipped with a magnetic stirrer and a reflux condenser. Toluene (30 mL per gram of anhydride) was added and to this stirred suspension was added the primary amine ($RNH_2$, 1 equivalent). The mixture then was heated to reflux with constant stirring for approximately 24 hours. At the end of this time, the 4-chloro-N-alkyl-1,8-naphthalimide might be obtained by cooling the reaction mixture and filtering the solid deposited. Recrystallization of this solid afforded the 4-chloro-N-alkyl-1,8-naphthalimide.

The 4-chloro-N-alkyl-1,8-naphthalimide (1 equivalent) was placed in a round-bottomed flask fitted with a magnetic stirrer and a reflux condenser, and sufficient of the second primary amine ($R'NH_2$) to dissolve all of the solid at 100° C. is added. The solution was heated to reflux with constant stirring for 24 hours, after which time the amine was removed by evaporation under reduced pressure. Recrystallization from methanol afforded the 4-alkylamino-N-alkyl-1,8-naphthalimide. When $R'NH_2$ corresponded to ethylenediamine, the product commonly crystallized as an indeterminate ethylenediamine solvate; several recrystallizations served to remove the excess ethylenediamine.

The synthesis of the 4-alkylamino-N-alkyl-1,8-naphthalimide was also carried out in a single operation by taking advantage of the dramatic rate differences in the rates of reaction between a primary amine and the anhydride and aryl chloride groups of the 4-chloro-1,8-naphthalic anhydride. In the one-pot procedure, the recrystallized anhydride (1 equivalent) was placed in a round-bottomed flask fitted with a magnetic stirrer, and the solid was suspended in 1,2-dimethoxyethane (DME, 30 mL per gram of anhydride). The resultant suspension was heated with constant stirring for 24 hours, the reaction mixture was then cooled, and the second primary amine ($R'NH_2$, 5 equivalents) was added. Heating was recommenced with constant stirring, and the reaction mixture was heated under reflux for a further 24 hours. The excess primary amine and the DME were removed by evaporation under reduced pressure, and the resultant fluorescent yellow solid was recrystallized from methanol.

Yields and physical properties are summarized in Table 2.

TABLE 2

Yields and Physical Properties of 4-Alkylamino-N-alkyl-1,8-naphthalimides.

| R | R' | Yield | m.p. |
|---|---|---|---|
| $CH_3(CH_2)_3$ | $CH_2CH_2NH_2$ | * | — |
| $CH_3(CH_2)_5$ | $CH_2CH_2OH$ | 95 | — |
| $CH_3(CH_2)_5$ | $CH_2CH_2NH_2$ | 73 | — |
| $CH_3(CH_2)_7$ | $CH_2CH_2NH_2$ | 92 | — |
| $CH_3(CH_2)_8$ | $CH_2CH_2NH_2$ | * | — |
| $CH_3(CH_2)_9$ | $CH_2CH_2NH_2$ | * | — |
| $CH_3(CH_2)_{11}$ | $CH_2CH_2NH_2$ | * | — |
| $CH_3(CH_2)_{13}$ | $CH_2CH_2NH_2$ | * | — |
| $CH_3(CH_2)_{15}$ | $CH_2CH_2NH_2$ | 76 | 76–78° C. |
| $CH_3(CH_2)_{17}$ | $CH_2CH_2NH_2$ | 77 | — |

* These compounds were obtained as non-stoichiometric ethylenediamine solvates. "Yields" were greater than 100% in all cases.

EXAMPLE 4-chloro-1,8-n-hexylnaphthalimide was produced as follows. 5.81 grams (0.0250 moles) of technical grade 4-chloro-1,8-napthalic anhydride purchased from Aldrich Chemical Company was placed in a 250 ml round bottom flask. The technical grade is approximately 95% pure with the major impurity being the 3-chloro isomer. 150 ml of toluene and 3.30 ml of hexyl amine (0.0250 moles) were added to the solution. The solution was refluxed until all solids dissolved, approximately 24 hours. The toluene was removed by rotary evaporation and the resultant solid was recrystallized from methanol and collected by vacuum filtration. 7.25 grams of 4-chloro-1,8-n-hexylnapthalimide was collected for a 92.0% yield. 10.1 grams (0.0320 moles) of the resultant 4-chloro-1,8-N-hexylnaphthalimide was placed in a 250 ml round bottom flask followed by 25 ml of ethylene diamine and the solution heated to reflux with stirring overnight. Excess ethylene diamine was removed by rotary evaporation and the solid recrystallized from methanol. The recrystallization yielded 12.5 grams of product wet with methanol for a 116% yield. NMR spectra of products were obtained on a 200 MHz Gemini NMR and were consistent with the proposed structure of the dye. FAB mass spectrometry was used to characterize the C-16 diamine dye. A molecular ion peak was observed at m/z=480 and other peaks were seen at m/z=256, 225, 213, 155, and 115.

Fluorescence spectra were obtained on a Gilford FLUOROIV spectrofluorometer using Corner House Software.

EXAMPLE 3

General Procedure for Metal Determination

A 1 ml of 10 μM dye was placed in a cuvette. 10 μL of a sample (oil or aqueous) was placed in the cuvette and the cuvette is mixed by inversion. The emission spectrum of the compound over the range of 600 to 460 nm was determined with a excitation wavelength between 420 and 450 nm. The ratio of fluorescence emission at approximately 490 and approximately 520 nm was determined. A standard curve was prepared using commercially available standards. The ratio of fluorescence emission was proportional to the concentration of the paramagnetic metals.

All fluorescence data were collected on a Gilford FLUOROIV using software from Corner House Software. Volga. S. Dak. Standards and other solutions of the dye and metal ions were generally made in isopropyl alcohol.

The quenching of the peak with an excitation max of 290 nm and an emission max at 490 or 520 nm indicated the presence of an f-block element (an element in the periodical table consisting of the lanthanoid series and the actinoid series). Thus, an f-block element can be distinguished from a d-block element (an element in the periodical table consisting of scandium, yttrium, and lanthanum together with the three periods of transition elements).

EXAMPLE 4

Dye standard solutions were made by dissolving the dye in distilled isopropyl alcohol to give a final dye concentration of 10 μM. Metal solutions were made by dissolving appropriate metal salts in isopropyl alcohol to give a useful metal concentration. Oil standards were produced by Constan Oil Company and contained alkyl sulfonates of 15 metal ions (Fe, Ag, Al, Cr, Cu, Mg, Na, Ni, Pb, Si, Sn, Ti, B, Mo, Au) in varying concentrations.

Real lubricating solutions were obtained from numerous internal combustion engines and were assayed for metal cation content by the following method. One hundred microliters of oil was dissolved in 10 ml of isopropyl alcohol and 0.1 ml of 1 mM dye was added and the solution shaken. This solution was placed in a cuvette and the fluorescent emission ratio of 490 to 520 nm was measured with an excitation wavelength of 450 nm.

The analyses of oil samples from internal combustion engines show that as both the vehicle and oil mileage increases, the amount of paramagnetic impurities in the oil increases. Table 3 shows the results of oil analyses of fleet vehicles. The results from Table 3 cannot be directly compared to the calibration curve in FIG. 3 as the base oils were different.

TABLE 3

| Vehicle | Vehicle Miles | Miles on Oil | Ratio |
|---|---|---|---|
| Aerostar | 14308 | 713 | 0.81 |
| Topaz | 14613 | 1360 | 0.90 |
| Escort | 1860 | 1860 | 0.84 |
| Taurus | 3694 | 3694 | 0.92 |

The foregoing has outlined rather broadly the features and technical advantages of the present invention in order that the invention which forms the subject of the claims of the invention may be better understood. It should be appreciated by those skilled in the art that the conception and the specific embodiment disclosed may be readily utilized as a basis for modifying or designing additional dyes and uses of those dyes that carry out the same purposes of the present invention. It should also be realized by those skilled in the art that such equivalent constructions do not depart from the spirit and scope of the invention as set forth in the appended claims.

What is claimed is:

1. The method of using a non-azo 1,8-naphthalimide dye for the detection or quantitation of a paramagnetic metal cation in a non-aqueous medium comprising: bringing into contact the non-azo 1,8-naphthalimide dye with the paramagnetic metal cation in the non-aqueous medium to form a mixture;

irradiating the mixture with a fluorescent light sufficient to cause the mixture to emit a detectable fluorescent emission spectrum;

detecting the fluorescent emission spectrum of the mixture; and, comparing the detected fluorescent emission spectrum with standard fluorescent emission spectra generated by reacting the non-azo 1,8-naphthalimide dye with different known amounts of the paramagnetic metal cations, wherein differences between the fluorescent emission spectra compared are dependent upon the presence or amount of the paramagnetic metal cation present in the mixture.

2. The method according to claim 1, wherein the dye-metal cation complex consists essentially of a stoichiometric complex.

3. The method according to claim 1, wherein the non-aqueous medium is a lubricant of a mechanical system.

4. The method according to claim 1, wherein the paramagnetic metal cation is selected from the group consisting of Fe, Cr, Cu, Ni, Ce, and Mn.

5. The method according to claim 1, wherein the concentration of paramagnetic metal cation is calculated using a fluorescent emission ratio of 490 to 520 nm and an excitation wavelength of about 450 nm.

6. The method according to claim 1, wherein the non-azo 1,8-naphthalimide dye bears substituents at the 3 and 4 positions with the group at the 3 position capable of functioning as a leaving group.

7. The method according to claim 1, wherein the non-azo 1,8-naphthalimide dye is a dimeric naphthalimide ring system.

8. A method for determining the presence or amount of a paramagnetic metal cation in a non-aqueous solution, comprising the steps of:
mixing a non-azo 1,8-naphthalimide dye with the paramagnetic metal cation in the non-aqueous solution to give a mixture;
irradiating the mixture with a fluorescent light sufficient to cause the mixture to emit a detectable fluorescent emission spectrum;
detecting the fluorescent emission spectrum of the mixture; and,
comparing the detected fluorescent emission spectrum with standard fluorescent emission spectra generated by reacting the non-azo 1,8-naphthalimide dye with different known amounts of the paramagnetic metal cations, wherein differences between the fluorescent emission spectra compared are dependent upon the presence or amount of the paramagnetic metal cation present in the mixture.

9. The method according to claim 8, whereby the mixture comprises a dye-metal cation complex.

10. The method according to claim 9, wherein the dye-metal complex consists essentially of a stoichiometric complex.

11. The method according to claim 8, wherein the non-aqueous solution is a lubricant of a mechanical system.

12. The method according to claim 8, wherein the paramagnetic metal cation is selected from the group consisting of Fe, Cr, Cu, Ni, Ce, and Mn.

13. The method according to claim 8, wherein the concentration of paramagnetic metal cation is calculated using a fluorescent emission ratio of 490 to 520 nm and an excitation wavelength of about 450 nm.

14. The method according to claim 8, wherein the non-azo 1,8-naphthalimide dye bears substituents at the 3 and 4 positions with the group at the 3 position capable of functioning as a leaving group.

15. The method according to claim 8, wherein the non-azo 1,8-naphthalimide dye is a dimeric naphthalimide ring system.

16. A naphthalimide compound having the formula which comprises mixtures of stereoisomers wherein R is an aliphatic alkyl group having C=4 to C=18; and R' is $(CH_2)_2NH_2$.

17. A method for determining the presence or amount of a paramagnetic metal cation in a non-aqueous medium, comprising the steps of:
mixing a naphthalimide compound, as recited in claim 16, with the paramagnetic metal cation in the non-aqueous medium to give a mixture;
irradiating the mixture with a fluorescent light of 450 nm to cause the mixture to emit a detectable fluorescent emission spectrum;
detecting a fluorescent emission ratio of 490 to 520 nm of the mixture; and,
monitoring differences in the detected fluorescent emission ratio of 490 to 520 nm of the mixture, as compared to standard fluorescent emission spectra ratio of 490 to 520 nm generated by reacting the naphthalimide compound, as recited in claim 16, with different known amounts of the paramagnetic metal cations, the differences being dependent upon the presence or amount of the paramagnetic metal cation present in the mixture.

18. A method for distinguishing an ion of an f-block element from an ion of a d-block element in a non-aqueous medium, comprising:
mixing a non-azo 1,8-naphthalimide dye with a non-aqueous solution containing the ion of the f-block or d-block element to give a mixture;
irradiating the mixture with a fluorescent light sufficient to cause the mixture to emit a detectable fluorescent emission spectrum;
detecting a fluorescent emission spectrum of the mixture; and
monitoring differences in the detected fluorescent emission spectrum of the mixture, as compared to standard fluorescent emission spectra generated by reacting the non-azo 1,8-naphthalimide dye with different known amounts of the ion of the f-block or d-block element, wherein the detection of quenching in the spectra indicates the presence of the ion of the f-block element.

* * * * *

UNITED STATES PATENT AND TRADEMARK OFFICE
CERTIFICATE OF CORRECTION

PATENT NO. : 5,308,773
DATED : May 3, 1994
INVENTOR(S) : Lewis et al.

It is certified that error appears in the above-indentified patent and that said Letters Patent is hereby corrected as shown below:

Col. 4, line 33, immediately following "ions", insert -- . --.

Col. 5, line 29, immediately following "490", insert -- and 527 --.

Col. 7, line 18, immediately following the heading "EXAMPLE", insert -- 2 --.

Signed and Sealed this

Twenty-fifth Day of July, 1995

Attest:

BRUCE LEHMAN

Attesting Officer     Commissioner of Patents and Trademarks